US011700889B2

(12) United States Patent
Buehler et al.

(10) Patent No.: US 11,700,889 B2
(45) Date of Patent: Jul. 18, 2023

(54) AEROSOL-GENERATING DEVICES INCORPORATING AN INTERTWINED WICK AND HEATING ELEMENT

(71) Applicant: Philip Morris Products S.A., Neuchatel (CH)

(72) Inventors: Frederic Buehler, Neuchatel (CH); Rui Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 601 days.

(21) Appl. No.: 16/684,416

(22) Filed: Nov. 14, 2019

(65) Prior Publication Data
US 2020/0077713 A1  Mar. 12, 2020

Related U.S. Application Data

(62) Division of application No. 15/126,907, filed as application No. PCT/EP2015/054978 on Mar. 10, 2015, now Pat. No. 10,512,283.

(30) Foreign Application Priority Data

Mar. 19, 2014  (EP) .................................. 14160717

(51) Int. Cl.
*A24F 40/44* (2020.01)
*A61L 9/03* (2006.01)
(Continued)

(52) U.S. Cl.
CPC ............ *A24F 40/44* (2020.01); *A24B 15/167* (2016.11); *A24F 40/46* (2020.01); *A24F 40/70* (2020.01);
(Continued)

(58) Field of Classification Search
None
See application file for complete search history.

(56) References Cited

U.S. PATENT DOCUMENTS 3,431,393 A * 3/1969 Yoshio ................ A01M 1/2077
239/57
5,161,646 A * 11/1992 Aurich ................ A01M 31/008
D22/125
(Continued)

FOREIGN PATENT DOCUMENTS

CA      2 943 996 A1   9/2015
CN       2095405 U    2/1992
(Continued)

OTHER PUBLICATIONS

Office Action dated Apr. 27, 2021 in corresponding Canadian Patent Application No. 2,937,278, 5 pages.
(Continued)

*Primary Examiner* — Thor S Campbell
(74) *Attorney, Agent, or Firm* — Oblon, McClelland, Maier & Neustadt, L.L.P.

(57) ABSTRACT

An aerosol-generating system is provided, including a heating element including a plurality of wires that are twisted together; and a capillary body, the capillary body being wound around the heating element. A method of manufacturing an aerosol-generating device is also provided, including providing a capillary body; twisting a plurality of wires together to form a heating element; and winding the capillary body around the heating element. The aerosol-generating system is advantageous in that the manufacturing process can be a fast and robust. The heater can be formed with high precision and consistency. Further, the heater and wick assembly are mechanically robust, allowing manual or auto-
(Continued)

matic handling without affecting its dimensions. This allows for a consistent quality of production.

14 Claims, 5 Drawing Sheets

(51) Int. Cl.
| | | |
|---|---|---|
| *A24F 40/46* | (2020.01) | |
| *A24F 40/10* | (2020.01) | |
| *A61L 9/14* | (2006.01) | |
| *A24F 40/70* | (2020.01) | |
| *A24B 15/167* | (2020.01) | |

(52) U.S. Cl.
CPC .............. *A61L 9/037* (2013.01); *A61L 9/14* (2013.01); *A24F 40/10* (2020.01)

(56) References Cited

U.S. PATENT DOCUMENTS

| | | | | |
|---|---|---|---|---|
| 5,196,171 | A * | 3/1993 | Peltier | B05B 5/0255 |
| | | | | 422/123 |
| 6,234,167 | B1 * | 5/2001 | Cox | A24F 40/30 |
| | | | | 128/200.14 |
| 9,301,547 | B2 * | 4/2016 | Liu | A24F 40/485 |
| 10,015,991 | B1 * | 7/2018 | Tucker | A24F 40/42 |
| 10,512,283 | B2 * | 12/2019 | Buehler | A24B 15/167 |
| 2009/0272379 | A1 | 11/2009 | Thorens et al. | |
| 2012/0145169 | A1 | 6/2012 | Wu | |
| 2013/0152922 | A1 | 6/2013 | Benassayag et al. | |
| 2013/0213419 | A1 | 8/2013 | Tucker et al. | |
| 2013/0228191 | A1 * | 9/2013 | Newton | A24F 40/44 |
| | | | | 131/329 |
| 2014/0000638 | A1 * | 1/2014 | Sebastian | A24F 40/50 |
| | | | | 131/328 |
| 2014/0209105 | A1 * | 7/2014 | Sears | A24F 40/44 |
| | | | | 131/328 |
| 2014/0318559 | A1 | 10/2014 | Thorens et al. | |
| 2015/0245669 | A1 * | 9/2015 | Cadieux | A24F 40/50 |
| | | | | 131/329 |

FOREIGN PATENT DOCUMENTS

| | | | |
|---|---|---|---|
| CN | 101004287 | A | 7/2007 |
| CN | 101358952 | A | 2/2009 |
| CN | 201223573 | Y | 4/2009 |
| CN | 101441178 | A | 5/2009 |
| CN | 101489686 | A | 7/2009 |
| CN | 201269841 | Y | 7/2009 |
| CN | 101516425 | A | 8/2009 |
| CN | 102014677 | A | 4/2011 |
| CN | 102103126 | A | 6/2011 |
| CN | 103237470 | A | 8/2013 |
| CN | 103338663 | A | 10/2013 |
| CN | 103338664 | A | 10/2013 |
| CN | 103338665 | A | 10/2013 |
| CN | 103512943 | A | 1/2014 |
| CN | 103529115 | A | 1/2014 |
| EP | 2 399 836 | A1 | 12/2011 |
| KR | 10-2012-0083828 | A | 7/2012 |
| KZ | 28018 | B | 12/2013 |
| RU | 2 389 419 | C2 | 5/2010 |
| RU | 2 425 608 | C2 | 8/2011 |
| RU | 107 026 | U1 | 8/2011 |
| WO | 2009/132793 | A1 | 11/2009 |
| WO | WO 2013/126777 | A2 | 8/2013 |
| WO | 2014/012894 | A1 | 1/2014 |
| WO | WO 2014/012905 | A1 | 1/2014 |
| WO | WO 2014/120479 | A1 | 8/2014 |
| WO | WO 2015/131058 | A1 | 9/2015 |

OTHER PUBLICATIONS

Combined Chinese Office Action and Search Report dated Apr. 2, 2021 in corresponding Chinese Patent Application No. 201910422186.2 (with English Translation), 18 pages.
Office Action dated Dec. 19, 2019 in Chinese Patent Application No. 2016-555282, 4 pages (with English translation).
International Search Report and Written Opinion dated Jun. 19, 2015 in PCT;EP15/054978 Filed Mar. 10, 2015.
Singaporean Office Action dated Jul. 17, 2017 in Patent Application No. 11201606342Y.
Combined Chinese Office Action and Search Report dated Sep. 28, 2018 in U.S. Appl. No. 201580011465.X, 10 pages (with English language translation).
Japan Office Action dated Jan. 31, 2019 in Japanese Patent Application No. 2016-555282 (with English translation), 15 pages.
Combined Russian Office Action and Search Report dated Apr. 22, 2022, issued in corresponding Russian Patent Application No. 2019101188 (with English Translation), 14 pages.
Korean Office Action dated Nov. 11, 2022 in Korean Patent Application No. 2022-7015828 filed on Mar. 10, 2015, with translation, total 8 pages.

\* cited by examiner

AEROSOL-GENERATING DEVICES INCORPORATING AN INTERTWINED WICK AND HEATING ELEMENT

CROSS-REFERENCE TO RELATED APPLICATIONS

This application is a divisional application of and claims the benefit of priority under 35 U.S.C. § 120 from U.S. application Ser. No. 15/126,907, filed on Sep. 16, 2016, which is a U.S. national stage application under 35 U.S.C. § 371 of PCT/EP2015/054978, filed on Mar. 10, 2015, and claims the benefit of priority under 35 U.S.C. § 119 from EP Application No. 14160717.6, filed on Mar. 19, 2014, the entire contents of each of which are incorporated herein by reference.

The present disclosure relates to aerosol generating systems that incorporate a heating element and capillary body, in which the capillary body is wound around the heating element or in which the heating element and capillary body are intertwined with one another. The disclosure also relates to methods of producing such heating element and wick assemblies.

Electrically heated smoking systems that are handheld and operate by heating a liquid aerosol-forming substrate in a capillary wick are known in the art. For example, WO2009/132793 describes an electrically heated smoking system comprising a shell and a replaceable mouthpiece. The shell comprises an electric power supply and electric circuitry. The mouthpiece comprises a liquid storage portion and a capillary wick having a first end and a second end. The first end of the wick extends into the liquid storage portion for contact with liquid therein. The mouthpiece also comprises a heating element for heating the second end of the capillary wick, an air outlet, and an aerosol-forming chamber between the second end of the capillary wick and the air outlet. The heating element is typically a coil of wire that is wound around the wick. When the shell and mouthpiece are engaged, the heating element is in electrical connection with the power supply via the circuitry, and a flow route for air is defined from at least one air inlet to the air outlet via the aerosol-forming chamber. In use, liquid is transferred from the liquid storage portion towards the heating element by capillary action in the wick. Liquid at the second end of the capillary wick is vaporised by the heating element. The supersaturated vapour created, is mixed and carried in the air-flow from the at least one air inlet to the aerosol-forming chamber. In the aerosol-forming chamber, the vapour condenses to form an aerosol, which is carried towards the air outlet into the mouth of a user.

FIG. 1 shows one example of an electrically operated aerosol generating system in accordance with the prior art having a liquid storage portion and a capillary body. A system of the type shown in FIG. 1 is disclosed in WO2009/132793. In FIG. 1, the system is a smoking system. The smoking system 100 of FIG. 1 comprises a housing 101 having a mouthpiece end 103 and a body end 105. In the body end, there is provided an electric power supply in the form of battery 107 and electric circuitry 109. A puff detection system 111 is also provided in cooperation with the electric circuitry 109. In the mouthpiece end, there is provided a liquid storage portion in the form of cartridge 113 containing liquid 115, a capillary body 117 and a heater 119. The heater is only shown schematically in FIG. 1, but typically comprises a coil of wire wrapped around the capillary body. In the exemplary embodiment shown in FIG. 1, one end of capillary wick 117 extends into cartridge 113 and the other end of capillary wick 117 is surrounded by the heater 119. The heater is connected to the electric circuitry via connections 121, which may pass along the outside of cartridge 113 (not shown in FIG. 1). The housing 101 also includes an air inlet 123, an air outlet 125 at the mouthpiece end, and an aerosol-forming chamber 127.

The heater coil is usually the main consumer of power in an electrically heated smoking system. Typically, electrically heated smoking systems apply an electrical current through the heater coil every time that the user puffs on the mouthpiece. This results in a very localized increase the temperature of the wick. It would be advantageous to provide a more efficient heating arrangement.

The specific characteristics of the wick and heater assembly are critical for achieving the required functional performance. Therefore, the ability to accurately and consistently produce wick and heater assemblies is crucial in any mass manufactured product. The wick and heater coil assembly requires sensitive handling during manufacture, due to its fragility. Typically, each wick is manually cut from a bobbin and is then manually assembled in the smoking system. The accuracy of the wick assembly is therefore highly human dependent.

The wicks also have poor mechanical strength but are required to be accurately placed and to remain in position for the required performance.

For a consistent performance of the smoking systems, and to reduce product-to-product variability in terms of final performance to the consumer, it is very important to have the heater coils produced with same dimensions, including the number and pitch of the coil turns, in all products. The manufacturing process used for current wick and heater coils, as well as the manual assembly, create failure modes for defects in the electrical coils, causing product-to-product variability, and therefore causing product-to-product performance variability.

It would be advantageous to provide a more robust heater and wick assembly suitable for use in electrical smoking systems and other aerosol-generating systems, that can be consistently produced.

In a first aspect, there is provided an aerosol-generating system comprising:
  a heater comprising at least one heating element; and
  a capillary body, wherein the capillary body is wound around the heating element.

The heating element and capillary body may be intertwined with one another. Intertwined in this context means joined by winding together.

An aerosol-generating system in accordance with the invention has the advantage that the manufacturing process can be a fast and robust process. The heater can be formed with high precision and consistency. Furthermore, the heater and wick assembly is mechanically robust, allowing manual or automatic handling without affecting its dimensions. This allows for a consistent quality of production.

Also, the greater surface contact between capillary body and heating element as compared with prior designs, means that, for an equivalent output of aerosol, the dimensions of the capillary body can be reduced, allowing for a reduction of the raw materials needed to produce the capillary body, and a reduction of related production costs.

The heating element may be helical wire. In one embodiment, both the heating element and the capillary body are helical.

The heating element may be a coil of electrically resistive wire. Alternatively, the heating element may be formed by stamping or etching a sheet blank that can be subsequently wrapped around a wick. In a preferred embodiment, the at least one heating element is a coil of electrically resistive wire. The pitch of the coil is preferably between 0.5 and 1.5 mm, and most preferably approximately 1.5 mm. The pitch of the coil means the spacing between adjacent turns of the coil. The coil may advantageously comprise fewer than six turns, and preferably has fewer than five turns. The electrically resistive wire advantageously has a diameter of between 0.10 and 0.15 mm, and preferably of approximately 0.125 mm. The electrically resistive wire is preferably formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America. The heating element may also comprise a metal foil, e.g., an aluminium foil, which is provided in the form of a ribbon.

The heating element may operate by resistive heating. In other words the material and dimensions of the heating element may be chosen so that when a particular current is passed through the heating element the temperature of the heating element is raised to a desired temperature. The current through the heating element may be applied by conduction from a battery or may be induced in the heating element by the application of a variable magnetic field around the heating element.

The aerosol-generating system may comprise a liquid storage portion containing liquid aerosol-forming substrate, wherein the capillary body is in contact with the liquid aerosol-forming substrate. The liquid storage portion and cover portion may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

The capillary body has two ends and both ends of the capillary body may be in contact with the liquid aerosol-forming substrate. Alternatively, only one end of the capillary body may be in contact with the liquid aerosol-forming substrate.

The aerosol-forming substrate is a substrate capable of releasing volatile compounds that can form an aerosol. The volatile compounds may be released by heating the aerosol-forming substrate. The aerosol-forming substrate is preferably a liquid aerosol-forming substrate and may contain nicotine. The aerosol-forming substrate may comprise plant-based material. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material.

The aerosol-forming substrate may comprise an aerosol-former. The aerosol-former may be any suitable known compound or mixture of compounds that, in use, facilitates formation of a dense and stable aerosol and that is substantially resistant to thermal degradation at the operating temperature of the aerosol-generating system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol-formers are polyhydric alcohols or mixtures thereof, such as triethylene glycol, 1,3-butanediol and, most preferred, glycerine.

The capillary material may comprise any suitable material or combination of materials which is able to convey the aerosol-forming substrate towards the vaporizer. The capillary material is preferably a porous material, but this need not be the case. The capillary material may have a fibrous or spongy structure. The capillary material preferably comprises a bundle of capillaries. For example, the capillary material may comprise a plurality of fibres or threads or other fine bore tubes. Alternatively, the capillary material may comprise sponge-like or foam-like material. The structure of the capillary material forms a plurality of small bores or tubes, through which the aerosol-forming substrate can be transported by capillary action from the storage portion towards the vaporizer. The particular preferred capillary material or materials will depend on the physical properties of the aerosol-forming substrate. Examples of suitable capillary materials include a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity so as to be used with different liquid physical properties. The liquid has physical properties, including but not limited to viscosity, surface tension, density, thermal conductivity, boiling point and vapour pressure, which allow the liquid to be transported through the capillary material. The capillary body may be formed from heat-resistant material.

Advantageously, the capillary body may comprise a plurality of fibre strands. The capillary body may comprise one or more first fibres having a longitudinally extending core section and a plurality of transverse sections extending transversely from the core section. The transverse sections may extend from opposite sides of the core section. The first fibres may each be formed from a ribbon of capillary material. The capillary body may further comprise one or more second fibres comprising a longitudinally extending core section but no transverse sections. The second fibres may have a larger cross-section than the first fibres.

Advantageously, the first and second fibres are together twisted around the heating element. The first and second fibres may be twisted together before being twisted around the heating element.

The second fibres may extend beyond the heating element, to contact with liquid in the liquid storage portion. The capillary body may be configured so that the first fibres do not extend into the liquid storage portion.

The heating element may comprise a plurality of wires that are twisted together. The capillary body may be held between the plurality of wires. The plurality of wires may be twisted together simultaneously with the step of winding the capillary body around the heating element.

A heater and capillary body assembly constructed in this way may provide a central airflow passage within the heating element as well as allowing for airflow around the exterior of the heating element. This improves the efficiency of the system as compared to prior designs.

The use of transverse elements encourages turbulent air flow across the heating element and capillary body, optimising the creation and dispersion of aerosol.

Electrical energy may be supplied to the heating element until the heating element reaches a temperature of between approximately 200° C. and 440° C. This is in contrast to conventional cigarettes in which the combustion of tobacco and cigarette wrapper may reach 800° C. Thus, the term "heat-resistant" in this specification refers to a material which is able to tolerate temperatures of more than approximately 200° C., or more preferably more than approximately 250° C., or even more preferably up to approximately 440° C., without noticeably degrading. An example of a suitable material is ceramic.

Preferably, the aerosol-generating system is hand held. The aerosol-generating system may be an electrically heated smoking system and may have a size comparable to a conventional cigar or cigarette. The smoking system may have a total length between approximately 30 mm and approximately 150 mm. The smoking system may have an external diameter between approximately 5 mm and approximately 30 mm.

The heating element and capillary body may be in a cartridge portion of the system, wherein the cartridge portion is configured to be coupled to a device portion of the system, the device portion including a power supply. The cartridge may be a single use item, which is disposed of after use. Alternatively, the cartridge portion may be refillable.

The aerosol generating device or cartridge may comprise at least one air inlet. The aerosol generating device or cartridge may comprise at least one air outlet. The aerosol generating device or cartridge may comprise an aerosol-forming chamber between the air inlet and air outlet so as to define an air flow route from the air inlet to the air outlet via the aerosol forming chamber, so as to convey the aerosol to the air outlet and into the mouth of a user. In embodiments in which the liquid storage portion comprises an interior passageway, preferably the air-flow route from the air inlet to the air outlet passes through the interior passageway. The aerosol-forming chamber simply assists or facilitates the generation of the aerosol.

The aerosol-generating system may be electrically operated, and may further comprise an electric power supply. The aerosol-generating system may further comprise electric circuitry. In one embodiment, the electric circuitry comprises a sensor to detect air-flow indicative of a user taking a puff. In that case, preferably, the electric circuitry may be arranged to provide an electric current pulse to the heating element when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

Preferably, the device or cartridge or system comprises a housing. Preferably, the housing is elongate. In one embodiment, the housing includes a removable insert comprising the liquid storage portion, the capillary body and the heating element. In that embodiment, those parts may be removable from the housing as a single component. This may be useful for refilling or replacing the storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

The longitudinal axis of the capillary body and heater assembly and the longitudinal axis of the housing may be substantially parallel. Alternatively, the longitudinal axis of the capillary body and heater assembly and the longitudinal axis of the housing may be substantially non-parallel, and may be perpendicular to one another.

An airflow passage may be defined within the heating element and capillary body, such that in use, air flows through the airflow passage to entrain vaporised substrate.

In a second aspect, there is provided: a method of manufacture: comprising providing a capillary body and a heating element; and winding the capillary body around the heating element.

The step of winding the capillary body around the heating element may comprise winding the capillary body and the heating element together to intertwine the capillary body and the heating element.

The capillary body may comprise a plurality of fibres of the same or different structure. The method may comprise twisting the fibres of the capillary body around one another. The step of twisting the fibres may be performed before winding the capillary body around the heating element or simultaneously with winding the capillary body around the heating element.

The capillary body may comprise one or more first fibres having a longitudinally extending core section and a plurality of transverse sections extending transversely from the core section. The transverse sections may extend from opposite sides of the core section. The first fibres may each be formed from a ribbon of capillary material. The capillary body may first comprise one or more second fibres comprising a longitudinally extending core section but no transverse sections. The second fibres may have a larger cross-section than the first fibres.

The method may comprise cutting the first fibres to a length corresponding to a length of the heating element.

The method may comprise twisting a plurality of wires together to form the heating element. The step of twisting a plurality of wires may be performed before winding the capillary body around the heating element or simultaneously with winding the capillary body around the heating element.

The method may comprise attaching the capillary body to a liquid storage portion. The step of attaching the capillary body to a liquid storage portion may comprise attaching the second fibres to the liquid storage portion.

The method may further comprise attaching the heating element to a supply of electrical power.

The method may comprise supplying a length of capillary body from a continuous supply of capillary body and supplying a length of heating element from a continuous supply of heating element, and cutting the length of capillary body from the supply of capillary body and cutting the length of heating element from the supply of heating element. The steps of cutting the length of capillary body and cutting the length of heating element may advantageously be performed after the step of winding the capillary body around the heating element together.

Features described in relation to one aspect of the invention may be applicable to another aspect of the invention.

Embodiments will now be described, by way of example only, with reference to the accompanying drawings, in which:

FIG. 3c is an end view of the assembly of FIG. 3a;

Figure 1:
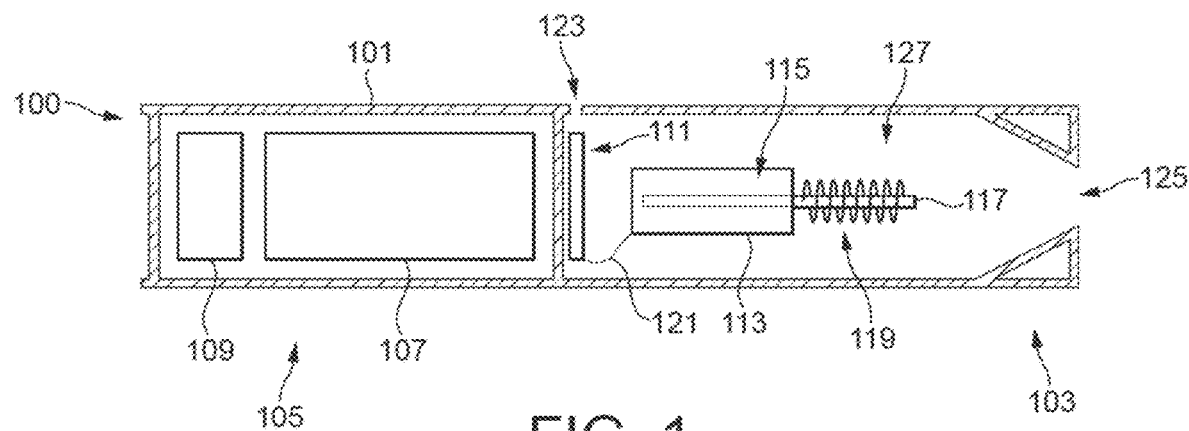
FIG. 1 is a schematic view of an aerosol-generating system in accordance with the prior art.

The system illustrated in FIG. 1 comprises a heating element 119, consisting of a coil of wire, wrapped around a capillary wick 117. As electrical current passes through the coil of wire, the wire heats up. Some of the heat generated in the wire is transferred to liquid substrate 115 within the capillary wick. That substrate 115 is thereby vaporised.

Figure 2:
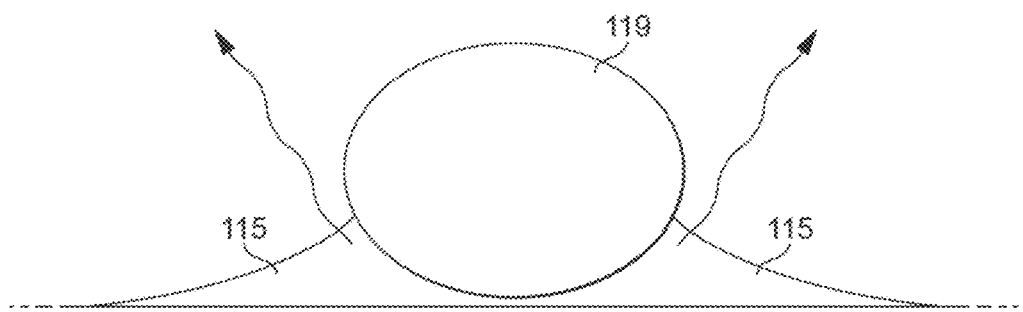
FIG. 2 is a schematic illustration of the contact between substrate and heating element in a system of the type shown in FIG. 1.

However much of the heat generated by passing current through the heating element is not transferred to the liquid substrate. FIG. 2 illustrates the area of contact between the liquid substrate 115 and heating element 119 in a system of the type shown in FIG. 1. Liquid substrate 115 in the capillary body forms a meniscus 118 that is drawn to the heating element. But it can be seen that less than half of the surface of the heating element 119 is in contact with the substrate 115. If a greater proportion of the surface of the heating element could be held in contact with the liquid substrate, then the system could be made more efficient. This would reduce the power required from the battery, which in turn would allow for the use of a smaller capacity battery with a quicker recharge time or for less frequent recharging or replacement of the battery.

Figure 3A:
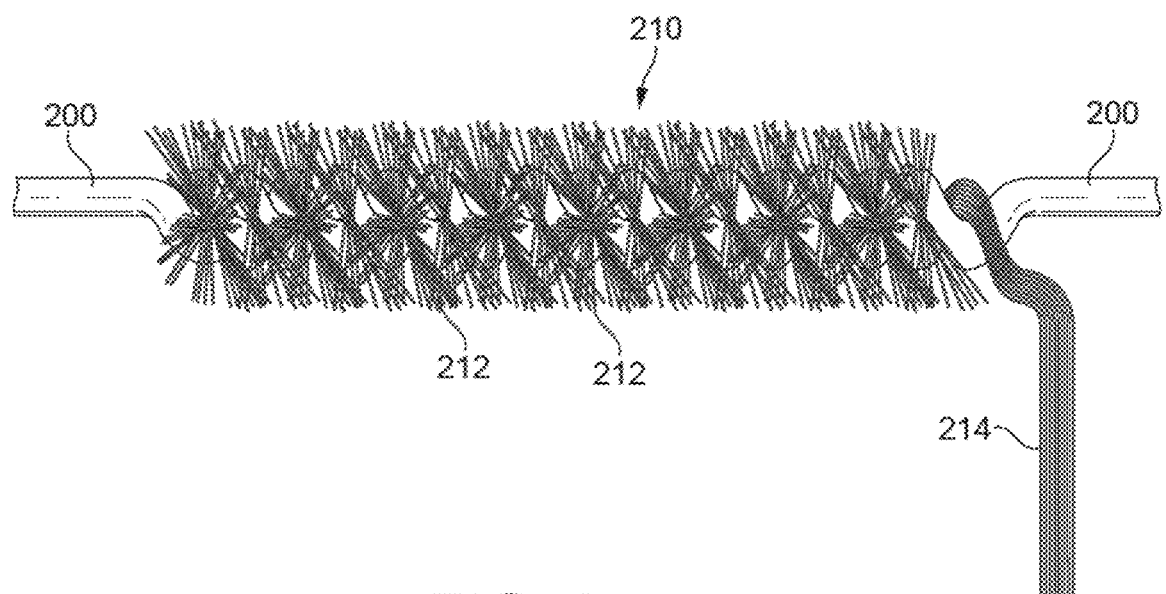
FIG. 3a shows a first example of a heating element and capillary body assembly in accordance with the invention.
Figure 3B:
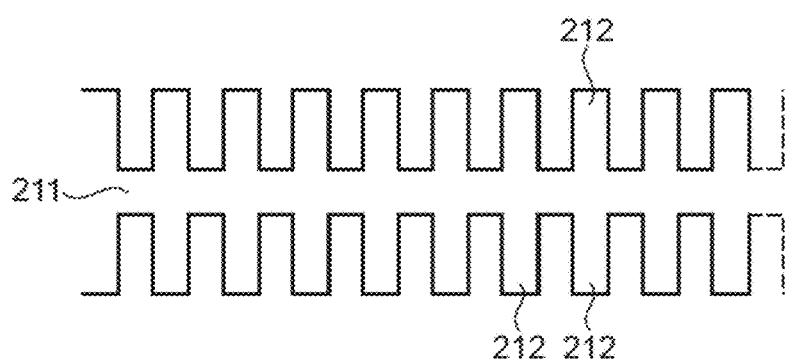
FIG. 3b shows the ribbon fibres with transverse sections that form part of the capillary body.

FIG. 3a shows a first example of a heating element and capillary body assembly in accordance with the invention. The heating element 200 is an electrically resistive wire formed into a helical configuration. The capillary body 210 is wound around the heating element. In the example shown in FIG. 3, the capillary body 210 comprises a plurality of separate fibre strands. Some of the fibre strands 211 have a longitudinally extending core section and a plurality of transverse sections 212 extending transversely from the core section. These fibre strands are initially flat, ribbon-like fibres, as shown in FIG. 3b. The transverse sections may be formed by transverse cuts in the ribbon to form a toothed structure or the edges of the ribbon may be profiled to create a plurality of transverse sections. The transverse sections extend from opposite sides of the core section.

The capillary body further comprises core fibres 214 have a larger cross-section than the ribbon fibres. The core fibres do not include transverse sections. The core fibres extend beyond the heating element so that they can extend into a liquid substrate that is to be heated.

Figure 3C:
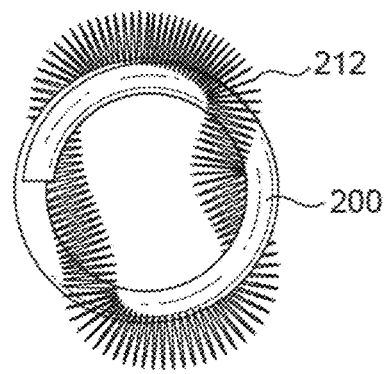

FIG. 3c is an end view of the heating element and capillary body assembly of FIG. 3a.

Figure 4:
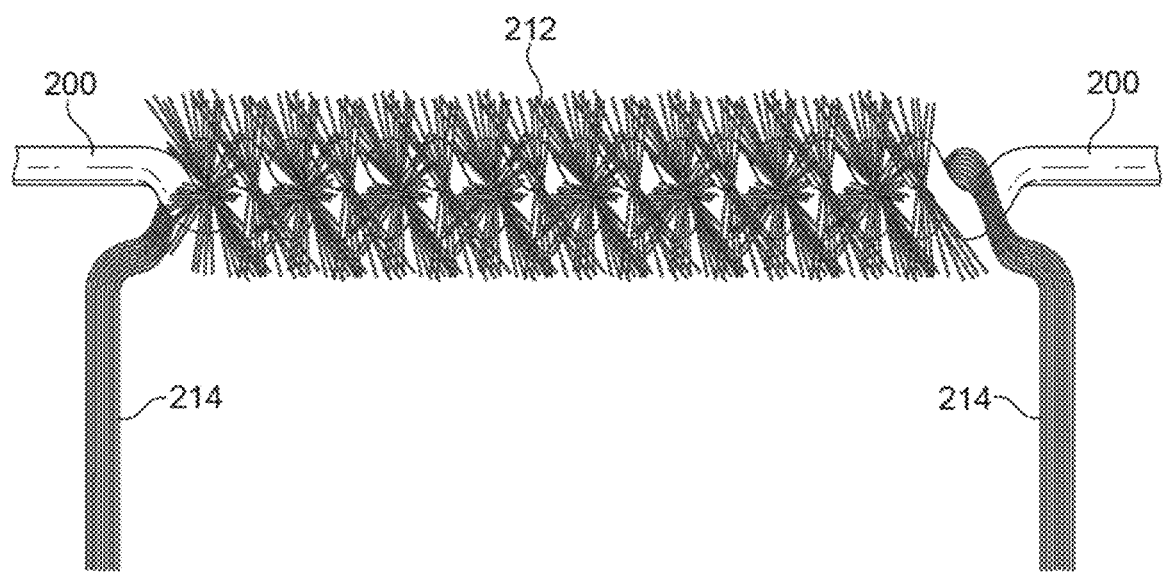
FIG. 4 shows a second example of a heating element and capillary body assembly in accordance with the invention.

FIG. 4 shows a second example of a heating element and wick assembly in accordance with the invention. The example shown in FIG. 4 is the same as that shown in Figure, except that that the core fibres 414 of the capillary body 210 extend from both ends of the helical heating element 200. If both ends of the capillary body are in contact with the same or different liquid storage portions, it allows liquid substrate to be conveyed to the heating element from both ends of the capillary body.

The heating element and capillary body assemblies illustrated in FIGS. 3a, 3b and 4 can be used in a system as illustrated in FIG. 1, with the capillary body, and in particular the core fibres, extending from a liquid storage portion 113. Alternative arrangements are also possible. In particular it is possible to arrange the heating element and capillary body assembly in any desired orientation relative to the air flow through the system.

Figure 5:
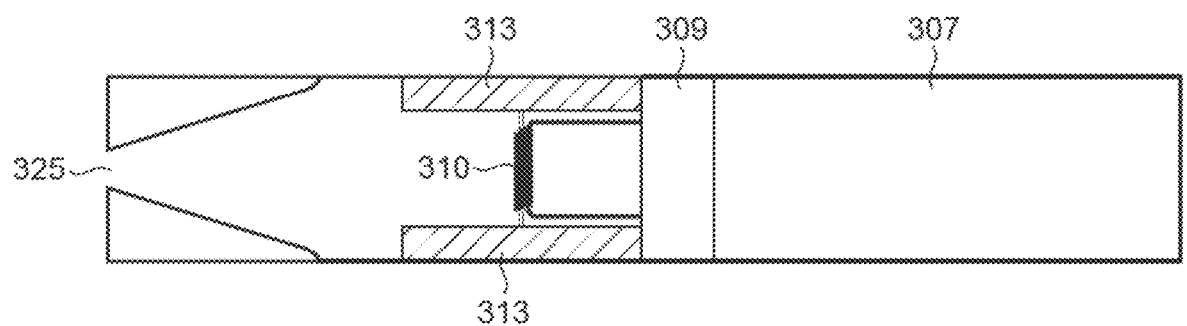
FIG. 5 is a schematic illustration of an aerosol-generating system in accordance with a first embodiment of the invention.

FIG. 5 is a schematic illustration of an aerosol-generating system in accordance with a first embodiment of the invention. In the embodiment of FIG. 5, the helical heating and capillary body assembly 310 element extends transverse to the direction of airflow through the system. In the embodiment shown in FIG. 5, the capillary body extends from both ends of the helical heating element, as illustrated in FIG. 4. The battery 307 provides power to the heating element 310 through control circuitry 309. The liquid storage portion 313 is annular and surrounds the heating element. Air is drawn through the system, past the heating element to entrain vaporised liquid substrate, by a user drawing on the mouthpiece 325.

Figure 6:
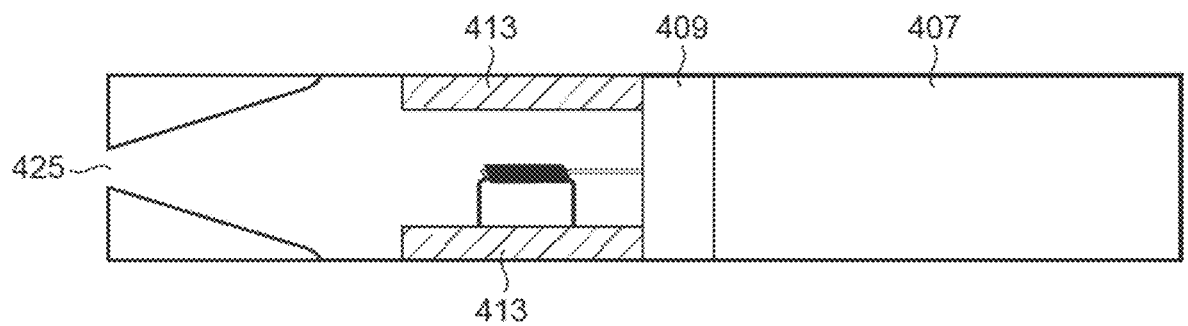
FIG. 6 is a schematic illustration of an aerosol-generating system in accordance with a second embodiment of the invention.

FIG. 6 is a schematic illustration of an aerosol-generating system in accordance with a second embodiment of the invention. In the embodiment of FIG. 6, the helical heating element extends parallel to the direction of airflow through the system. The battery 407 provides power to the heating element 410 through control circuitry 409. The liquid storage portion 413 is annular and surrounds the heating element. Air is drawn through the system, past the heating element to entrain vaporised liquid substrate, by a user drawing on the mouthpiece 425.

Figure 7:
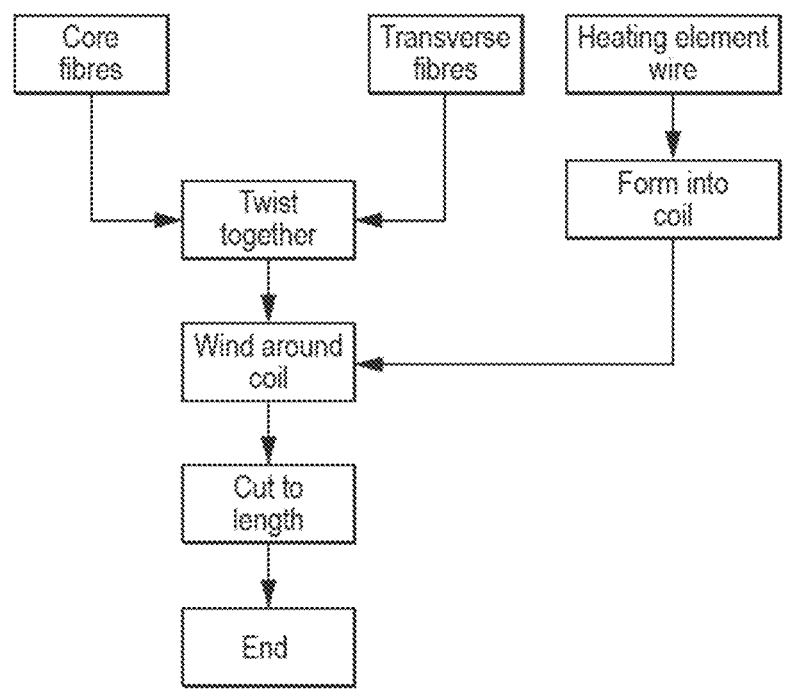
FIG. 7 is a schematic diagram illustrating a manufacturing process for a heating element and capillary body assembly in accordance with the invention.

FIG. 7 is a schematic diagram illustrating a manufacturing process for a heating element and wick assembly in accordance with the invention.

The invention claimed is:

1. An aerosol-generating system, comprising:
   a heating element comprising a plurality of wires that are twisted together, the heating element having a longitudinal axis and a plurality of turns; and
   a capillary body,
   wherein the capillary body is wound around an interior and an exterior of the heating element, and
   wherein the plurality of turns of the heating element define a central passage extending substantially parallel to the longitudinal axis of the heating element.

2. The aerosol-generating system according to claim 1, wherein the heating element and the capillary body are intertwined with one another.

3. The aerosol-generating system according to claim 1, wherein the heating element is helical.

4. The aerosol generating system according claim 1, wherein the capillary body is helical.

5. The aerosol-generating system according to claim 1, further comprising a liquid storage portion containing liquid aerosol-forming substrate, wherein the capillary body is in contact with the liquid aerosol-forming substrate.

6. The aerosol-generating system according to claim 5, wherein the capillary body has two ends, and wherein the two ends of the capillary body are in contact with the liquid aerosol-forming substrate.

7. The aerosol-generating system according to claim 5, wherein the liquid aerosol-forming substrate contains nicotine.

8. The aerosol-generating system according to claim 1, wherein the system is an electrically heated smoking system.

9. The aerosol-generating system according claim 1, wherein the capillary body comprises a fibre comprising a plurality of strands.

10. The aerosol-generating system according to claim 9, wherein the plurality of strands comprise one or more first fibres having a longitudinally extending core section and a plurality of transverse sections extending transversely from the core section.

11. The aerosol-generating system according to claim 10, wherein the capillary body further comprises one or more second fibres comprising a longitudinally extending core section but no transverse sections.

12. The aerosol-generating device according to claim 1, further comprising an airflow passage within the heating element and the capillary body.

13. A method of manufacturing an aerosol-generating device, comprising:
   providing a capillary body;
   twisting a plurality of wires together to form a heating element, the heating element having a longitudinal axis and a plurality of turns; and
   winding the capillary body around an interior and an exterior of the heating element,
   wherein the plurality of turns of the heating element define a central passage extending substantially parallel to the longitudinal axis of the heating element.

14. The method according to claim 13, wherein the winding comprises winding the capillary body and the heating element together to intertwine the capillary body and the heating element.

* * * * *